United States Patent [19]

Hirth et al.

[11] Patent Number: 5,156,977
[45] Date of Patent: Oct. 20, 1992

[54] MONOCLONAL ANTIBODIES AGAINST ATRIAL, NATRIURETIC PEPTIDES OF HUMANS, HYBRIDOMAS & METHODS OF USE

[75] Inventors: Caludia Hirth; Frank-Joachim Morich, both of Wuppertal; Dieter Neuser, Wuelfrath; Johannes-Peter Stasch, Wuppertal, all of Fed. Rep. of Germany

[73] Assignee: Bayer Aktiengesellschaft, Leverkusen, Fed. Rep. of Germany

[21] Appl. No.: 323,527

[22] Filed: Mar. 14, 1989

Related U.S. Application Data

[63] Continuation of Ser. No. 838,640, Mar. 11, 1986, abandoned.

[30] Foreign Application Priority Data

Mar. 20, 1985 [DE] Fed. Rep. of Germany ....... 3509958

[51] Int. Cl.⁵ .......................................... G01N 33/531
[52] U.S. Cl. ..................................... 436/548; 435/7.1; 435/172.2; 435/240.27; 436/547; 530/806; 530/388.24; 530/388.25
[58] Field of Search ................... 436/547, 548; 435/7, 435/172.2, 240.27, 103, 110; 530/387, 806, 827; 935/103, 110

[56] References Cited

U.S. PATENT DOCUMENTS

| | | | |
|---|---|---|---|
| 4,376,110 | 3/1983 | David | 436/548 |
| 4,451,570 | 5/1984 | Royston | 435/240 |
| 4,596,769 | 6/1986 | Shockman | 436/548 |
| 4,656,158 | 4/1987 | Matsuo et al. | 514/12 |
| 4,657,891 | 4/1987 | Matsuo et al. | 514/11 |
| 4,659,678 | 4/1987 | Forrest | 436/822 |
| 4,666,829 | 5/1987 | Glenner | 436/548 |

FOREIGN PATENT DOCUMENTS 8504870 11/1985 World Int. Prop. O. .

OTHER PUBLICATIONS

Prowse et al—J. of Immunological Methods vol. 118 (1989) pp. 91–100.
Cohen—Scientific American vol. 258 (Apr. 1988) pp. 34–42.
McKenzie et al.—J. Histochem & Cytochem vol. 33 (1985) pp. 828–832.
Chapeau et al—Histochem & Cytochem vol. 33 (1985) pp. 541–550.
Lerner et al—Scientific American vol. 258 (Mar. 1988) pp. 42–50.
Nakao, et al., "Radioimmunoassay for α-human & rat ANP, Brochem. & Bio Phys. Res. Comm.", vol. 124, No. 3, 1984, pp. 815–821.
Sevier, et al., "Monoclonal Antibodies in Clinical Immunology", Clinical Chem., Nov. 27, 1981, pp. 1797–1806.
Lang et al.—Nature vol. 314 (Mar. 21, 1985) pp. 264–266.
Tanaka et al—Biochem & Biophysical Research Communications vol. 124, No. 2 (1984) pp. 663–668.
Atlas et al—Nature vol. 309 (Jun. 21, 1984) pp. 717–719.
Lang: Nature 314, pp. 264–266, (1985).
Chapeau: Chemical Abstracts 103: 17493f (1985).
McKenzie; Chemical Abstracts 103:99430v (1985).
Atlas: Nature 309, pp. 717–719, (1984).
Tanaka: Biochem & Biophys. Res. Comm. 124(2) pp. 663–668 (1984).
Milne: Molecular Immunology 24(2) pp. 127–132 (1987).

Primary Examiner—Sam Rosen
Attorney, Agent, or Firm—Sprung Horn Kramer & Woods

[57] ABSTRACT

Monoclonal antibodies against atrial, natriuretic peptides are produced by deposited hybridoma cell lines 85031401 and 85031402 deposited with the European Collection of Animal Cell Cultures. The hybridoma are produced by fusion with cells from mammals which produce antibodies against atrial natriuretic peptides. The antibodies can thereafter be used in assays for the determination of the level of artrial natriuretic peptides in biological samples such as blood, plasma, serum, urine, lymph or cerebrospinal fluid.

8 Claims, 3 Drawing Sheets

MONOCLONAL ANTIBODIES AGAINST ATRIAL, NATRIURETIC PEPTIDES OF HUMANS, HYBRIDOMAS & METHODS OF USE

This is a continuation of application Ser. No. 06/838,640, filed Mar. 11, 1986, now abandoned.

The invention relates to generally new hybridoma cell lines, in particular hybridoma cell lines which produce monoclonal antibodies (mAb) with specificity for atrial, natriuretic peptides (ANP), especially those of humans and of rats, and to the use as a diagnostic aid and for research purposes both in vivo and in vitro of the mAb as produced in this manner.

The fusion of mouse myeloma cells with spleen cells from immunized mice (Köhler and Milstein, Nature 256, 495–497 (1975)) was the first indication of the possibility of obtaining continuous cell lines which produce uniform (called "monoclonal") antibodies. Since then, numerous attempts have been made to prepare various hybrid cells (called "hybridoma") and to use the antibodies formed by them for various scientific investigations (for example: Current Topics in Microbiology and Immunology, Vol. 81—"Lymphocyte Hybridomas", F. Melchers et al., Springer Verlag, 1978 and references therein; C. Barnstable et al., Cell 14, 9–20 (1978); P. Parham, W. F. Bodmer, Nature 276, 397-399, Handbook of Experimental Immunology, 3rd edition, volume 2, D. M. Wier, Editor, Blackwell 1978, chapter 25; Chem. Eng. News, 15–17 (1979) 9). These publications describe the principal techniques for the production of monoclonal antibodies by hybridomas.

Monoclonal antibodies against histocompatibility antigens, against haptens, proteins and enzymes have been produced. However, as yet no monoclonal antibody which highly selectively reacts with atrial, natriuretic peptides of mammals, such as, for example, those of humans or rats, is known.

The atrial, natriuretic peptides are a group having different chain lengths, whose minimum active sequence consists of 23 amino acids. Peptides which additionally contain other N-terminal and C-terminal amino acids are likewise active. The peptides are produced by the actions of enzymes in the atrium of the heart from a precursor molecular of about 152 amino acids. The gene coding for ANP has been cloned, and the DNA has been sequenced.

The ANPs induce short-lasting but potent natriuresis, it not having been possible as yet to prove an exact tubular site of attack of the substances. In addition, ANPs are potent vasodilators which, inter alia, may antagonize the vasoaction of noradrenaline, angiotensin II, histamine and serotonin. The effect of ANPs is not abolished by indomethacin, which makes it improbable that the effect takes place via endogenous prostaglandin synthesis. Hypotensive effects of ANP in two-clip hypertensive rats and SH rats have been described.

In isolated cells, an inhibitory effect on the secretion of aldosterone and vasopressin has been detected. It is possible using conventional antibodies to measure radioimmunologically the plasma levels of ANP, which depend on the volume status of the particular experimental animal. Specific binding to isolated zona glomerulosa cells has been detected using a $^{125}$iodine-labelled ANP derivative. Initial experiments indicate that ANP induces release of kallikrein in the kidney. Under certain conditions, the kidney activity of the peptides can be abolished by pretreatment with haloperidol (for review see Sagnella and MacGregor, Nature 399, 666–668, 1984). The activity spectrum of ANP makes it very probable that these peptides are involved, casually or symptomatically, in circulatory disorders (hypertension, hypotension, arteriosclerosis), in cardiac disorders (acute and chronic cardiac insufficiency, myocardial infarct, cardiac arrhythmias, coronary heart disease) and in kidney disorders (acute and chronic renal insufficiency during the course of various basic disorders, uraemia), Thus, quantitative determination of ANP in various biological body fluids (for example blood, plasma, serum, urine, lymph or in the cerebrospinal fluid) will attain great importance for all the syndromes mentioned.

Some of the plasma levels of ANP measured using conventional antisera are very high, which may be explained by the cross-reactivity or lack of specificity of these antibodies. The risk of determination of falsely high plasma levels of atrial, natriuretic peptides can be eliminated by the use of highly specific (monoclonal) antibodies. Hence, antibodies of this type would be ideally suited for the diagnosis of all disorders associated with a change in the ANP level.

The present invention relates to the preparation of hybridoma cell lines which synthesize and secrete highly specific monoclonal antibodies against atrial, natriuretic peptides. The invention also relates to hybridoma cell lines which synthesize and secrete monoclonal antibodies against atrial, natriuretic peptides of mammals, in particular against those of humans or rats. The hybridomas are prepared by the method of Köhler and Milstein mentioned in the introduction. After immunization of mice with atrial, natriuretic peptides which are bound to an immunogenic carrier such as, for example, protein, the spleen cells of these mice are fused with cells of a mouse myeloma cell line. The hybridomas resulting from this are systematically examined for antibodies which selectively react with the atrial, natriuretic peptides. In this way, hybridomas which produce antibodies against atrial, natriuretic peptides have been isolated. The invention also relates to these antibodies.

Hybridomas which produce these antibodies have been deposited at the National Collection of Animal Cell Cultures, PHLS Centre for Applied Microbiology and Research, Porton Down, Salisbury SP4 OJG, UK, under deposition numbers 8503/402 (hybridoma cell line which produces the mAb 11A-A11) and 8503/402 (hybridoma cell line which produces the mAb 23 M-D9).

The antibodies according to the invention can be used, for example, for the determination of the levels of atrial, natriuretic peptides in biological fluids such as, for example, blood, plasma, serum, urine, lymph or the cerebrospinal fluid. The antibodies according to the invention are particularly well suited for the production of immunoassays. However, they can also be used for the isolation of atrial, natriuretic peptides using immunoadsorption chromatography.

Animal experimental investigations are absolutely necessary for research into the significance of ANP under various physiological and pathophysiological conditions. The prerequisite for these studies and for all studies on the pharmacology of ANP is that there are specific and sensitive assays for quantitative determination in body fluids.

The antibodies according to the invention can be used, for example, for the determination of the levels of atrial, natriuretic peptides in the serum of experimental animals for diagnostic purposes. The antibodies according to the invention are also very well suited for physiological or pharmacological experiments.

The preparation of the hybridomas comprises, in general, the following steps:

A) Immunization of mammals with atrial, natriuretic peptide, such as, for example, from humans or rats, which is bound to an immunogenic carrier, in particular to an immunogenic carrier protein (for example keyhole limpet hemocyanin) (KLH-ANP). Female Balb/c mice have proved to be suitable for this purpose, but it is also possible to use other strains of mice. The immunization regimen and the concentrations of KLH-ANP should be chosen so that an adequate number of antigen-stimulated lymphocytes is formed. Three immunizations at intervals of 14 days with 100 ug of KLH-ANP mouse by injection in phosphate-buffered physiological saline have proved to be effective.

B) Obtaining the spleen of the immunized mammals (for example mice) and preparation of a spleen cell suspension in a suitable medium. About 1 ml of medium per spleen is sufficient. The experimental techniques for this are known.

C) Fusion of the suspended spleen cells with myeloma cells of a suitable cell line (for example mouse myeloma PX63Ag8), by use of a suitable fusion promoter (for example polyethylene glycol). Preferred fusion promoters are polyethylene glycols of mean molecular weight between 1,000 and 4,000 (for example commercially available PEG 1,000 etc.). However, it is also possible to use other known fusion promoters. The preferred spleen cells/myeloma cells ratio is about 10. A total volume of about 0.5–1.0 ml of fusion medium is sufficient for $10^8$ spleen cells. Many mouse myeloma cells are known and can be obtained from, for example, scientific institutes or cell depository institutions. The cell line which is used should preferably have a genetic defect so that non-fused myeloma cells die in a selection medium whereas hybrids survive. The cell lines used most frequently are those which are resistant to 8-azaguanine and which lack the enzyme hypoxanthine guanine phosphoribosyltransferase, and which thus are unable to grow in an HAT medium (hypoxanthine, aminopterin, thymidine) (Science 145:709, 1964).

The myeloma cell line which is used should preferably also be of the non-secreting type, so that it does not itself form antibodies or H- or L-chains of immunoglobulins. However, in some cases secreting myeloma cells may be an advantage.

D) The fusion mixture (spleen cells and myeloma cells) is diluted and cultivated in a selective medium in individual vessels so that the non-fused cells do not multiply and die within 1–2 weeks. The individual fused cells are isolated by adjusting the volume of the diluent so that a certain number of cells (about 1–4) is placed in each individual vessel (for example each well of a microtiter plate).

E) Testing for the presence of antibodies against atrial, natriuretic peptides in each vessel.

F) Selection and cloning (for example by limiting dilution) of the hybridomas which produce the desired antibody.

Once the desired hybrodima has been selected and cloned it is possible to produce the antibody by two different ways. Monoclonal antibodies of very high purity are obtained when the hybridomas are cultivated in a suitable medium for a certain time and the antibody is obtained from the supernatant. A suitable medium and the optimum culture time are straightforward to determine. This in vitro technique provides monoclonal antibodies which are contaminated by only small amounts of proteins from the heterologous serum (for example fetal calf serum).

In order to prepare a considerably higher concentration of monoclonal antibodies of only slightly lower purity, it is possible to inject the selected hybridoma intraperitoneally into a mouse—preferably one which is syngeneic or semisyngeneic. After an incubation time, this leads to the formation of a tumor in the mouse, which releases high concentrations of antibody (5–20 mg/ml) in the blood and in the peritoneal exudate (ascites) of the host animal. Even if these mice have normal antibodies in the blood and in the ascites, nevertheless their concentration is very low compared with the mAb. The monoclonal antibody thus obtained has a very high titre (it is active in dilutions of $10^{-3}$ or below), and the ratio between specific and non-specific immunoglobulin is about 20:1.

The invention will be further described in the following illustrative examples in conjunction with the accompanying drawings wherein.

EXAMPLE 1

Figure 1:
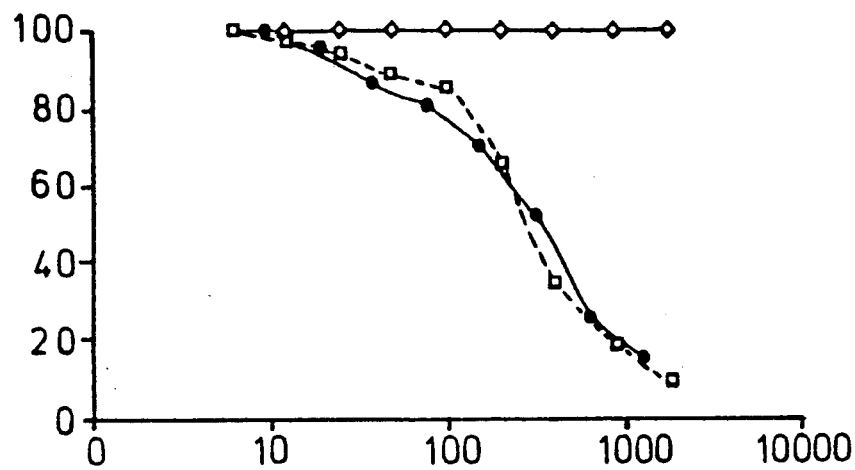
FIG. 1 is a calibration curve for the displacement of radioactively labelled antigen from mAb 23M-D9 by various atriopeptins and their derivatives.

Preparation of Monoclonal Antibodies Against Atrial, Natriuretic Peptides of Humans and Rats Preparation of the antigen used for the immunization The antigen used was a conjugate of human α-ANP or atriopeptin II of the rat (supplied by Bachem) and keyhole Limpet hemocyanin (KLH, Pacific Biomarine Supply Company). For the preparation, KLH and human α-ANP or atriopeptin II were mixed in a molar ratio of 1:1 and, at a concentration of 2 mg/ml in phosphate-buffered physiological saline, glutaraldehyde was added. The final concentration of glutaraldehyde in the reaction mixture was 0.25%. After incubation at room temperature for one hour, the protein conjugates were dialyzed several times against phosphate-buffered physiological saline at 4° C.

Immunization of Balb/c mice

Female Balb/c mice were immunized intraperitoneally with 100 μg of KLH-ANP conjugate in 0.2 ml of complete Freund's adjuvant. 14 days later, the animals again received 100 μg of the antigen introperitoneally in incomplete Freund's adjuvant. Two further intravenous immunizations are carried out at 14-day intervals with 50 μg of antigen in 100 μg of phosphate-buffered saline/animal each time. The spleens of the animals were removed three days after the last administration of antigen.

Preparation of a spleen cell suspension

Individual cell suspensions were prepared from the removed spleens by forcing the organs through a stainless steel sieve. The cells were transferred into Dulbecco's minimal essential medium (DMEM) which was supplemented with 4.5 g/l glucose, 100 unit/l penicillin and 100 μg/ml streptomycin. The cells were washed 3 times with DMEM and then resuspended in the desired concentration in the same medium. In general, about $10^8$ cells were obtained from each spleen.

Preparation of the myeloma cells

The myeloma cell line X63Ag8.653 used for this is a subclone of the mouse myeloma cell line P3-X63-Ag8, which does not express any heavy or light chains of immunoglobulins (J. Immunol. 123:1543–1550 (1980)). The cells are sensitive to 20 μg/ml 8-azaguanine and are no longer able to grow in a medium which contains hypoxanthine, aminopterin and thymidine (HAT). They were cultivated in DMEM which was supplemented with 4,5 g/l of glucose, 20 mM glutamine, 1,000 units/ml penicillin, 100 μg streptomycin and 10% fetal calf serum (complete medium). At the time of fusion the myeloma cells were in the logarithmic phase of cell multiplication.

Cell fusion

The spleen cell suspensions were added to the myeloma cells in DMEM without serum with a ratio of 10:1, and centrifugation was carried out in round-bottomed cups at 200 g for 10 min. After sedimentation of the cells, the supernatant was carefully decanted off. The cells were incubated with 2 ml of a solution of polyethylene glycol of molecular weight 2,000 (diluted to 30% w/w with DMEM, pH 7.6) at 37° C. for 1 min. Then 20 ml of DMEM were added, whereupon the cells were carefully resuspended for a few minutes. They were again centrifuged at 200 g for 5 min, and the cell pellet was resuspended in HAT medium at a concentration of $10^6$ cells/ml, whereupon they were distributed in 1 ml portions in Costar plates.

Selection and culturing of the hybridomas

After cell fusion, the cells were cultivated in HAT medium (hypoxanthine, aminopterin, thymidine) at 37° C. with 5% $CO_2$ in a moist atmosphere. After a few weeks, supernatants from hybridoma cell cultures were investigated for the presence of anti-ANP activity using the appropriate enzyme immunoassay (see below). Those hybridoma cell lines which showed positive results in the anti-ANP assay were selected for cloning.

This entailed the hydridomas being subjected to a limiting dilution technique, in which a mean of 0.5 cells/well were distributed over 96 microtitre wells, $10^5$ mouse thymocytes per well being added as "feeder cells". The cells which still produced anti-ANP antibody after this cloning process were multiplied, frozen and stored in liquid nitrogen in complete medium which contained 25% fetal calf serum and 7.5% dimethyl sulphoxide.

Preparation of large amounts of monoclonal antibodies

Mice which had been pretreated by intraperitoneal injection of 0.5 ml of pristane received intraperitoneal injections of cloned hybridomas in order to be able to obtain ascites fluid containing antibodies after about 10 to 15 days. The antibody activity in the ascites fluid was determined in a radioactive binding inhibition assay (see Example 3).

Determination of the anti-ANP activity in culture supernatants

100 μl of culture supernatant were added to microtitre plates onto which a conjugate of bovine serum albumin and human α-ANP or atriopeptin II of the rat (5 μg/ml) had been absorbed at room temperature for 3 hours, and which had been then washed 5 times with water. Rabbit anti-mouse immunoglobulin which was coupled to peroxidase was then added; the plates were subsequently incubated at room temperature for 2 hours. After having been washed 5 times with distilled water, a substrate buffer suitable for the enzyme was added, and the concentration of the resulting colored product was determined using a photometer suitable for microtitre plates.

EXAMPLE 2

Characterization of the Monoclonal Antibody Against Atrial, Natriuretic Peptides Typing of the monoclonal antibody The classes and subclasses of the monoclonal antibody described here were analyzed. The antibody was enriched from the culture supernatant and partially purified by precipitation with ammonium sulphate (40% saturation). The immunoglobin class were determined in an Ouchterlony gel diffusion test using class-specific anti-mouse immunoglobulin antisera. The monoclonal antibody 23M-D9 against human ANP belongs to the $IgG_1$ class. The monoclonal antibody 11A-A11 against atriopeptin II likewise belongs to the $I_gG_1$ class.

Cross-reaction of the antibody with various other peptides and hormones

The cross-reactivity of the monoclonal antibody against human ANP with various other peptides was determined using a radioimmunological binding inhibition assay. The assay is carried out in a special assay buffer (0.02M sodium phosphate; 0.15M NaCl; 0.01% thiomersal; 0.1% gelatin; 0.01% BSA and 0.1% triton-X 100, pH 7.4). Radioactively labelled $^{125}$iodine-α-human-ANP (amino acids 1–28) from humans or $^{125}$iodine-atriopeptin II of the rat (Amersham Buchler) are incubated together with antibodies in suitable dilution at 4° C. for 16–48 hours. The total volume is 500 μl. In the binding inhibition assay, the assay mixture additionally contains, at the same volume, unlabelled antigen or the various inhibitors in different concentrations. At the end of the incubation, the radioactively labelled $^{125}$iodine-antigen (human α-ANP with aminoacids 1–28 or atriopeptin III of the rat) which is not bound to the antibody is adsorbed onto charcoal by addition of a suspension of active charcoal (0.2M sodium phosphate; 2% norit A active charcoal; 0.02% dextran 60; 0.1% BSA and 10 mM $Na_2$EDTA, pH 7.4) followed by incubation on ice for 20 min. The active charcoal is then sedimented by centrifugation at 3,600 g for 10 min, and the radioactivity in the supernatant is determined. Measurement was carried out of the concentration of various peptides which is necessary to displace 50% of the $^{125}$iodine-antigen from the antibody. As is evident from FIGS. 1 and 2, the antibodies react highly specifically with atrial peptides from humans and rats. No cross-reactivities with other mediators involved in the regulation of the salt-water balance were detectable. A variety of vasoactive substances were equally inactive (see Tables 1 and 2).

EXAMPLE 3

Use of the Monoclonal Antibody against Atrial, Natriuretic Peptides

Detection of ANP immunoreactivity in biological fluids and tissues using the monoclonal antibody Antigens in high dilution can be determined quantitatively using a radioimmunoassay. Highly specific antibodies and a radioactively labelled antigen are necessary for this assay. The binding of the radioactively labelled antigen to the antibody can be dose-independently inhibited by non-radioactive antigen. If various defined concentrations of non-radioactive antigen are incubated with constant concentrations of antibodies and radioactively labelled antigen it is possible in this way to draw up a characteristic calibration curve. FIG. 1 shows a calibration curve of this type, specifically for the displacement of radioactively labelled antigen ($^{125}$iodine-human-alpha-ANP, amino-acids 1-28) from mAb 23M-D9 by various atriopeptins or their derivatives. This entailed the binding of the radioactive antigen to the antibody in % being plotted against the concentration of non-labelled antigen or its fragments in fmol/ml.

The assay was carried out as described in the text with ascites fluid in a final dilution of 1:1,500,000. The assay with culture supernatant provides similar results, merely the dilution which can be used being a factor of 500 to 1,000 less. This experiment shows clearly that the ANP fragment (amino acids 18-28) is not able to displace the radioactively labelled antigen from the antibody. Thus, the antibody has no cross-reactivity with this fragment. Unknown amounts of antigen in solution can be determined using this calibration curve. A radio-immunoassay based on the monoclonal antibody which is described here and $^{125}$iodine-human-$\alpha$-ANP (amino acids 1-28) as tracer makes possible detection in biological fluids and tissue extracts down to a concentration of 20 pg/ml, which corresponds approximately to an amount of 6 fmol/ml (see FIG. 1).

Figure 2:
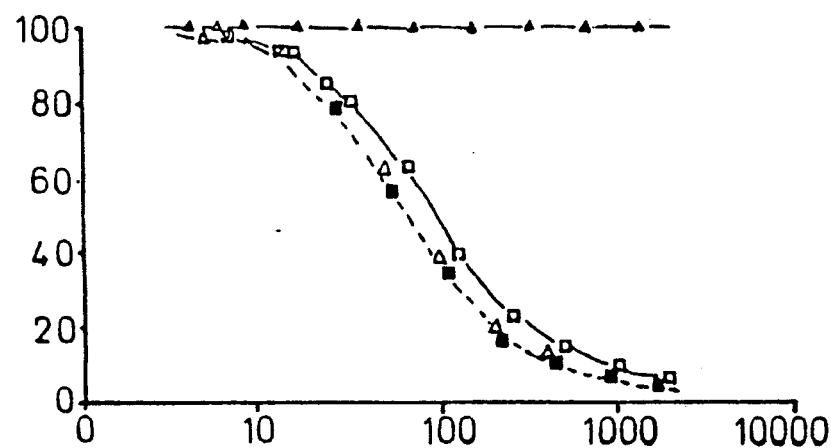
FIG. 2 is a calibration curve for the displacement of radioactively labelled antigen from mAb 11A-A11 by various atriopeptins and a fragment.

FIG. 2 shows an experiment carried out in the same way on the mAb 11A-A11, which reacts specifically with atriopeptin of rats.

The mode of plotting is the same as for FIG. 1.

The assay was carried out as described in the text with ascite fluid in a final dilution of 1:1,250,000. The assay on culture supernatant provides similar results, merely the dilution which can be used being a factor of 500 to 1,000 less. This experiment shows clearly that the ANP fragment (amino acids 13-28) is not able to displace the radioactively labelled antigen from the antibody. Thus, the antibody has no cross-reactivity with this fragment. Unknown amounts of antigen in solution can be determined using this calibration curve. A radio-immunoassay based on the monoclonal antibody which is described here and $^{125}$iodine-atriopeptin III as tracer makes possible detection in biological fluids and tissue extracts down to a concentration of 20 pg/ml, which approximately corresponds to an amount of 6 fmol/ml (see FIG. 2). In addition to the radio-immunological process presented here, it is also possible to carry out other types of immunoassay (for example ELISA, chemiluminescence, fluorescence) using the monoclonal antibodies described.

EXAMPLE 4

Antagonism of the In Vivo Effects of Atriopeptin of Rats

Use was made of male Wistar rats (body weight 240-270 g) which were fasted from the evening before the day of the experiment but had free access to drinking water. The preparation and the experiment were carried out under inactin anaesthesia (100 mg/kg i.p.). After tracheotomy and injection of 1 mg/kg atropine i.p., a plastic catheter was tied into the femoral artery for measurement of the blood pressure, a plastic catheter was tied into the jugular vein for injection or infusion of solutions, and a bladder catheter was inserted. When preparation was complete, the rats received an injection of 5 ml/kg 0.9% strength NaCl solution and then, for the duration of the experiment, an infusion of the same solution (1.2 ml/hour). The rectal temperature of the experimental animals was maintained at 37°±1° C. by a heat lamp. After a 1-hour equilibration time had elapsed, the urine was collected in preweighed vessels which were changed after each 10 or 20 min. The concentrations of Na$^+$ and K$^+$ in the urine were determined by flame photometry (Instrumentation Laboratory, Lexington, Mass./USA). The antibody fluid contained 100 $\mu$l of sterile-filtered ascites fluid and 0.1% bovine serum albumin in 1 ml of 0.9% strength NaCl solution. Synthetic atriopeptin II (supplied by Bachem) was likewise injected in aqueous solution containing 0.9% NaCl and 0.1% bovine serum albumin. The injection volume was 1 ml/kg body weight in all cases. Preliminary experiments had shown that a bolus injection of 1 ml/kg body weight of 0.9% strength NaCl solution containing 0.1% bovine serum albumin has only a slight effect on the volume of urine and the excretion of sodium. After completion of the experiments, an arterial blood sample was taken from each rat to check the acid-base status.

10 $\mu$g/kg atriopeptide II lead, in the first 10 min after i.v. bolus injection, to a large increase in the volume of urine and excretion of sodium (see FIGS. 3 and 4). In the subsequent collection periods, this increase rapidly diminishes and, after one hour, can be reproduced well by renewed i.v. bolus injection of 10 $\mu$g/kg body weight of ANP. The increase in the volume of urine and the excretion of sodium can be almost completely suppressed by bolus injection of 100 $\mu$l/kg body weight of antibody-containing ascites fluid (antibody 11A-A11) 5 min before the second injection of ANP.

Figure 3A:
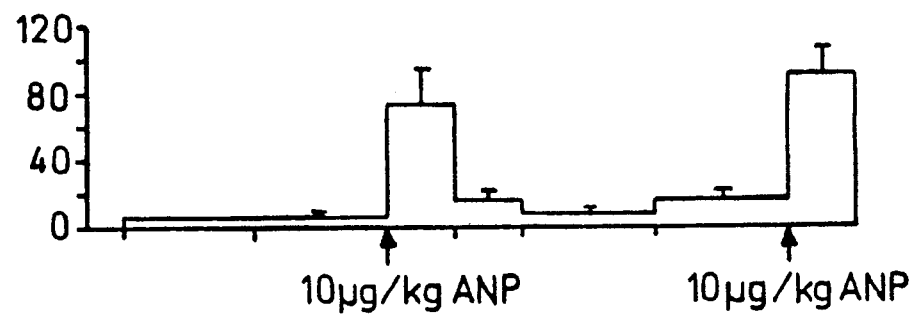
FIGS. 3a and 3b are plots of urine excreted against time.
Figure 3B:
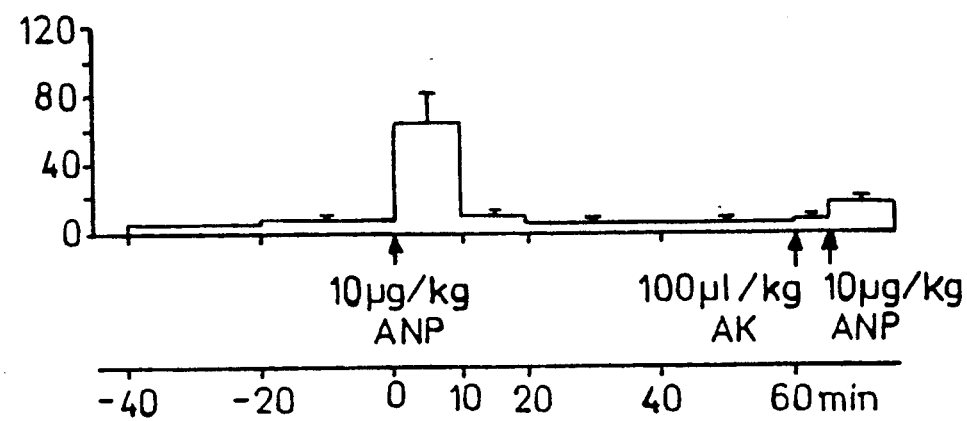
Figure 4A:
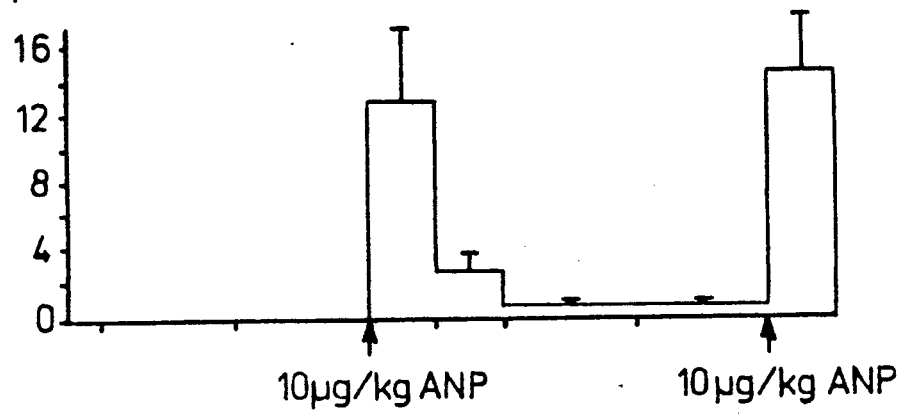
FIGS. 4a and 4b are plots of sodium excreted against time.
Figure 4B:
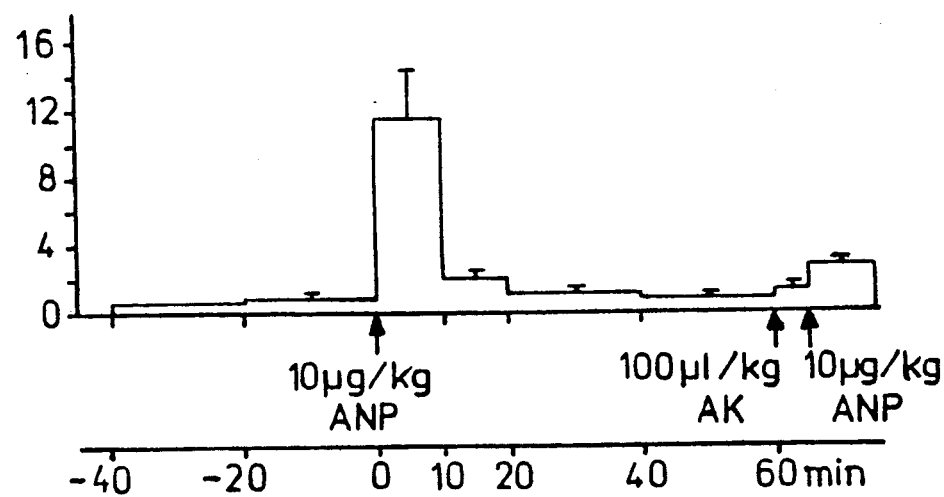

FIGS. 3 and 4 show the results in detail. The collection time (collection periods) in minutes is plotted on the ordinate against the excretion of urine in $\mu$l/min (FIGS. 3a and 3b) and the excretion of sodium in $\mu$mol/min (FIGS. 4a and 4b).

FIG. 3a: volume of urine after two bolus injections of 10 $\mu$g/kg atriopeptin II (ANP), n=4

FIG. 3b: antagonism of the effect of 10 $\mu$g/kg atriopeptin II by mAb against ANP: 5 min before the second injection of ANP, a bolus injection of 100 $\mu$l/kg antibody-containing ascites fluid (Ab) was given, n=4

FIG. 4a: excretion of sodium after two bolus injections of 10 $\mu$g/kg atriopeptin II (ANP), n=4

FIG. 4b: antagonism of the effect of 20 $\mu$g/kg atriopeptin II by mAb against ANP: 5 min before the second injection of ANP, a bolus injection of 100 $\mu$l/kg antibody-containing ascites fluid (Ab) was given, n=4.

Thus the antibodies antagonize the natriuretic effect of atriopeptin II in vivo.

TABLE 1

Investigation of the cross-reactivity of mAb 23.M-D9 with other endogenous mediators having vasoactivity or with effects on the salt-water balance

| Substance | Max. tested conc. (pmol/ml) | Cross-reactivity |
|---|---|---|
| Angiotensin II (human) | 14 | — |
| Leu-enkephalin | 26 | — |
| Substance P | 10 | — |
| Aldosterone | 44 | — |
| ACTH (pig) | 4 | — |

TABLE 1-continued

Investigation of the cross-reactivity of mAb 23 M-D9 with other endogenous mediators having vasoactivity or with effects on the salt-water balance

| Substance | Max. tested conc. (pmol/ml) | Cross-reactivity |
| --- | --- | --- |
| Bradykinin | 13 | — |
| μ-MSH | 10 | — |
| Insulin (rat) | 3 | — |
| Vasopressin | 15 | — |
| Renin (pig) | 0.5 | — |

TABLE 2

Investigation of the cross-reactivity of mAb 11A-A11 with other endogenous mediators having vasoactivity or with effects on the salt-water balance

| Substance | Max. tested conc. (pmol/ml) | Cross-reactivity |
| --- | --- | --- |
| Angiotensin II (human) | 14 | — |
| Leu-enkephalin | 26 | — |
| Substance P | 10 | — |
| Aldosterone | 44 | — |
| ACTH (pig) | 4 | — |
| Bradykinin | 13 | — |
| μ-MSH | 10 | — |
| Insulin (rat) | 3 | — |
| Vasopressin | 15 | — |
| Renin (pig) | 0.5 | — |

It will be appreciated that the instant specification and examples are set forth by way of illustration and not limitation, and that various modifications and changes may be made without departing from the spirit and scope of the present invention.

We claim:

1. Monoclonal antibodies against atrial, natriuretic peptides of mammals with said antibodies having no cross-reactivity with other endogenous mediators having vasoactivity or having effects on the salt-water balance.

2. Monoclonal antibodies according to claim 1 wherein the mediator is selected from the group consisting of
   Angiotensin II,
   Leu-enkephalin,
   Substance P,
   Aldosterone,
   ACTH,
   Bradykinin,
   U-MSH,
   Insulin,
   Vasopressin and
   Renin.

3. Monoclonal antibodies according to claim 1, produced by hybridoma cell line 85031401 deposited with the European Collection of Animal Cell Cultures.

4. Monoclonal antibodies according to claim 1, produced by hybridoma cell line 85031402 deposited with the European Collection of Animal Cell Cultures.

5. A process for the determination of the presence of atrial natiuretic peptides of mammals in a biological sample comprising contacting said sample with monoclonal antibodies according to claim 1, incubating said sample with the antibodies to allow binding of the antibodies with the atrial natriuretic peptide, and determining the amount of the antibody bound to the peptide.

6. The process according to claim 5, wherein the sample is blood, plasma, serum, urine, lymph or cerebrospinal fluid.

7. Hybridoma cell line 85031401 deposited with the European Collection of Animal Cell Cultures.

8. Hybridoma cell line 85031402 deposited with the European Collection of Animal Cell Cultures.

* * * * *

UNITED STATES PATENT AND TRADEMARK OFFICE
CERTIFICATE OF CORRECTION

PATENT NO. : 5,156,977

DATED : October 20, 1992

INVENTOR(S) : Claudia Hirth, et al.

It is certified that error appears in the above-identified patent and that said Letters Patent is hereby corrected as shown below:

Title Page          [75] Inventors: 1st inventor, delete "Caludia" and substitute -- Claudia --

Signed and Sealed this

Tenth Day of May, 1994

*Attest:*

BRUCE LEHMAN

*Attesting Officer*    *Commissioner of Patents and Trademarks*